United States Patent [19]

Nilsson

[11] Patent Number: 4,800,897
[45] Date of Patent: Jan. 31, 1989

[54] DEVICE FOR DETECTION OF RELATIVE MOVEMENTS AND/OR POSITIONS OF A PART OF THE BODY OR THE LIKE

[75] Inventor: Sten Nilsson, Göteborg, Sweden
[73] Assignee: SE-Produkter, Sweden
[21] Appl. No.: 30,869
[22] PCT Filed: Jun. 24, 1986
[86] PCT No.: PCT/SE86/00304
    § 371 Date: Feb. 24, 1987
    § 102(e) Date: Feb. 24, 1987
[87] PCT Pub. No.: WO87/00026
    PCT Pub. Date: Jan. 15, 1987

[30] Foreign Application Priority Data

Jun. 24, 1985 [SE] Sweden ................................ 8503151

[51] Int. Cl.⁴ .............................................. A61B 5/10
[52] U.S. Cl. ........................................ 128/782; 128/78
[58] Field of Search ................ 128/76 R, 78, 303 B,
    128/303 R, 774, 781, 782; 33/1 M, 1 N, 1 CC,
    1 PT, 511, 512; 340/678

[56] References Cited

U.S. PATENT DOCUMENTS

| 2,796,866 | 6/1957 | Cohen | 128/303 R |
| 2,930,133 | 3/1960 | Thompson | 33/512 |
| 3,955,562 | 5/1976 | Farrar | 128/782 |
| 4,306,571 | 12/1981 | McLeod | 128/782 |
| 4,436,099 | 3/1984 | Raftopoulus | 128/782 |
| 4,477,973 | 10/1984 | Davies . | |
| 4,485,825 | 12/1984 | Domjan et al. | 33/512 |
| 4,486,955 | 12/1984 | Fizter et al. | 33/1 PT |
| 4,528,990 | 7/1985 | Krowles | 128/774 |
| 4,539,979 | 9/1985 | Brener | 128/78 |
| 4,571,834 | 2/1986 | Fraser et al. | 33/1 PT |
| 4,586,515 | 5/1986 | Berger | 128/782 |

FOREIGN PATENT DOCUMENTS 562269 8/1977 U.S.S.R. .

OTHER PUBLICATIONS

"Wrist and Shoulder Motion Analyzer", Little et al., Research Disclosure, Nov. 1981.
Soviet Union Abstract, 85-67, 356/11 Su 1109-128-A (Derwent) Aug. 23, 1984.

Primary Examiner—Max Hindenburg
Attorney, Agent, or Firm—Ostrolenk, Faber, Gerb & Soffen

[57] ABSTRACT

Device for detection of relative motions or positions of one or more parts of the body, comprising at least two measuring sensors which are applied to the parts of the body whose motions or positions are to be measured. Signals from the sensors are transmitted to a signal processor for storing and/or analyzing. The measuring sensors are connected to the fulcrums of a parallelogram action linkage which is attached to the parts of the body whose relative movements or positions are to be detected. The imaginary axes about which some of the above-mentioned motions take place form a part of the parallelogram action linkage.

9 Claims, 11 Drawing Sheets

MATRIX
HEAD ROTATION    FLEXION

|    | 0 | 1 | 2 | 3 | 4 | EX |
|----|---|---|---|---|---|----|
| EX | 0 | 0 | 0 | 0 | 0 | 0  |
| 6  | 0 | 0 | 0 | 0 | 0 | 0  |
| 5  | 0 | 0 | 0 | 0 | 0 | 0  |
| 4  | 1 | 5 | 0 | 0 | 0 | 0  |
| 3  | 1 | 3 | 2 | 0 | 0 | 0  |
| 2  | 4 | 4 | 2 | 0 | 0 | 0  |
| 1  | 1 | 7 | 5 | 3 | 2 | 2  |
| 0  | 2 | 0 | 3 | 2 | 3 | 10 |
| 1  | 0 | 0 | 2 | 3 | 2 | 11 |
| 2  | 1 | 1 | 0 | 0 | 0 | 0  |
| 3  | 0 | 1 | 1 | 0 | 0 | 0  |
| 4  | 0 | 0 | 0 | 0 | 0 | 0  |
| 5  | 1 | 3 | 0 | 1 | 0 | 0  |
| 6  | 0 | 2 | 1 | 0 | 0 | 0  |
| EX | 0 | 0 | 0 | 0 | 0 | 0  |

BACK ROTATION

| POSITION | NO | % |
|----------|----|----|
| 9 | 0 | 0 |
| 8 | 0 | 0 |
| 7 | 0 | 0 |
| 6 | 0 | 0 |
| 5 | 0 | 0 |
| 4 | 3 | 1 |
| 3 | 14 | 5 |
| 2 | 47 | 18 |
| 1 | 22 | 8 |
| 0 | 35 | 13 |
| 1 | 66 | 25 |
| 2 | 73 | 28 |
| 3 | 4 | 2 |
| 4 | 0 | 0 |
| 5 | 0 | 0 |
| 6 | 0 | 0 |
| 7 | 0 | 0 |
| 8 | 0 | 0 |
| 9 | 1 | 0 |

FIG. 8g

MATRIX
BACK ROTATION FLEXION

|   | 0  | 1 | 2 | 3 | 4 | EX |
|---|----|---|---|---|---|----|
| EX| 0  | 0 | 0 | 0 | 0 | 1  |
| 8 | 0  | 0 | 0 | 0 | 0 | 0  |
| 7 | 0  | 0 | 0 | 0 | 0 | 0  |
| 6 | 0  | 0 | 0 | 0 | 0 | 0  |
| 5 | 0  | 0 | 0 | 0 | 0 | 0  |
| 4 | 3  | 0 | 0 | 0 | 0 | 0  |
| 3 | 14 | 0 | 0 | 0 | 0 | 4  |
| 2 | 53 | 0 | 0 | 0 | 0 | 61 |
| 1 | 73 | 0 | 0 | 0 | 0 | 15 |
| 0 | 17 | 0 | 0 | 0 | 0 | 18 |

DEVICE FOR DETECTION OF RELATIVE MOVEMENTS AND/OR POSITIONS OF A PART OF THE BODY OR THE LIKE

The present invention relates to a device for detection of relative movements or positions of one or more parts of the body, comprising at least two measuring sensors which are attached to the part/parts of the body the movements/positions of which are to be measured, by which signals are emitted to a signal processor for storing and/or analyzing.

BACKGROUND OF THE INVENTION

There is a great demand for studies and analyzes of body movements during different working moments, e.g. in industry. The most important reason is to prevent pains and injuries, e.g. in the back and the neck, where they are very frequent. Another reason is that the law of "occupational injury insurance" requires that mechanical stresses, that a person have been exposed to in an occupational injury, have to be estimated.

Today, it is common that physiotherapists or industrial hygienists visit working places and study in which way the different working movements are performed, and thereby this knowledge is increased and makes it possible to take steps to decrease the presence of injuries and pain, which is very high in different exposed working places. By studying for example how many times and for how long a part of a body is in a special position, a base is obtained to give the size of the stress for different working movements and this makes it possible to give advice and if necessary restrictions for performing the working movements.

THE PRIOR ART

Many devices for detection of movement or position of a part of the body are known today. These are based on different registration techniques. For example, film-cameras or video cameras can be used for registration of a working movement. But the evaluation of the film if quite time- and work-consuming. Important limitations also appear when the film is taken; thus, the technique can be used only in a few cases.

Another known technique is based on opto-electronics, where e.g. an infrared-camera is used to detect a number of points of light which are attached on the object. Because of the disadvantage that the points of light have to be exposed to the camera all the time, this method is not suitable for measurements in real working places where some movements might be hidden by machines or likewise. The evaluation in this case requires also a lot of work.

The most suitable technique for detection of movements or positions of a working person (the test object) is the goniometer technique. This technique means that some kind of sensing member is constructed, e.g., an angular sensing member, which physically detects the movements or the position of the part of the body and converts this to e.g. an electrical signal which is proportional to the movement or position. The quantity of information is processed/reduced in order to make it possible to present it in an easily readable way.

An example of the goniometer technique is described in the Swedish Pat. No. 7900887-7 which presents a device for measuring the position of a part of the body in relation to the earth's gravitation. It is not possible to measure e.g. the bending of a part of the body in relation to another, with this device.

Another registration device is shown in U.S. Pat. No. 4,306,571. Herein, a three-plane measuring device comprising three potentiometers which are arranged to measure the rotation of a knee in three axes or planes is described. For example, square shafts are used for mechanical transmission of torsional or rotational movements. But the field of application for this device is not the same as for the present invention. That is, it is only intended to make measurements of a knee, which is only one joint and cannot be compared with a complex system like a back, a neck, etc.

In U.S. Pat. No. 4,436,099 there is further shown a measuring device which is suitable e.g. for measuring of angular changes between a person's upper arm and forearm. With this device it is possible to measure angular movements only in one plane, which movements are converted optically by a disc having segments of different colours, said disc being caused to rotate in either direction. The apparatus cannot be used for detection of movements of the back and the head.

OBJECTS AND SUMMARY OF THE INVENTION

The object of the present invention is to provide a device for detection of relative motions or positions of a part of the body, and in which device the aforementioned disadvantages are eliminated, and which makes simple and accurate measurings even of complicated movement systems such as the back, neck or likewise possible at a relatively low cost. The invention is provided by the fact that the measuring sensor is placed in connection with the fulcrums of a parallelogram action linkage attached to the parts of the body, the relative movements or positions of which are to be detected, and where the imaginariy axes around about which one or some of said movements are performed form a part of the parallelogram action linkage.

BRIEF DESCRIPTION OF THE DRAWINGS

The invention will in the following be described with reference to an embodiment shown in the accompanying drawings.

FIGS. 8a-8g show examples of transcriptions from the measuring device, in which FIG. 8a shows an example of a transcription in the form of a histogram and a table illustrating the frequency of different positions of back flexion of a test person; FIGS. 8(b), 8(c), 8(d) and 8(f) show the same for head lateral flexion, head flexion, head rotation and back rotation, respectively; and FIGS. 8(e) and 8(g) are matrices of head rotation-flexion and back rotation-flexion, respectively, showing the number of occasions a certain position simultaneously is taken; the measurements being taken according to the ranges illustrated in FIGS. 7(a)–7(c).

DESCRIPTION OF AN EMBODIMENT

Figure 1A:
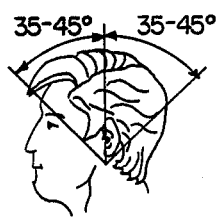
FIGS. 1(a-f) show the different types of bending/rotations which the present invention is intended to measure.
Figure 1B:
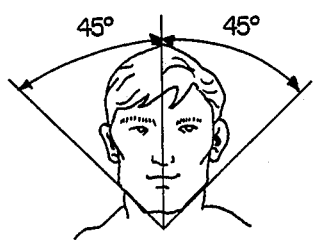
Figure 1C:
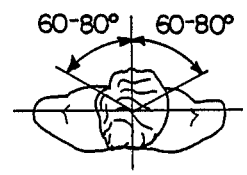
Figure 1D:
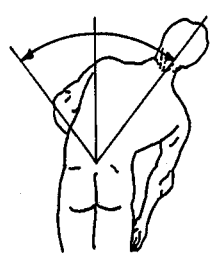
Figure 1E:
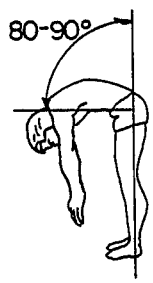
Figure 1F:
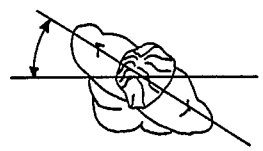
Figure 2:
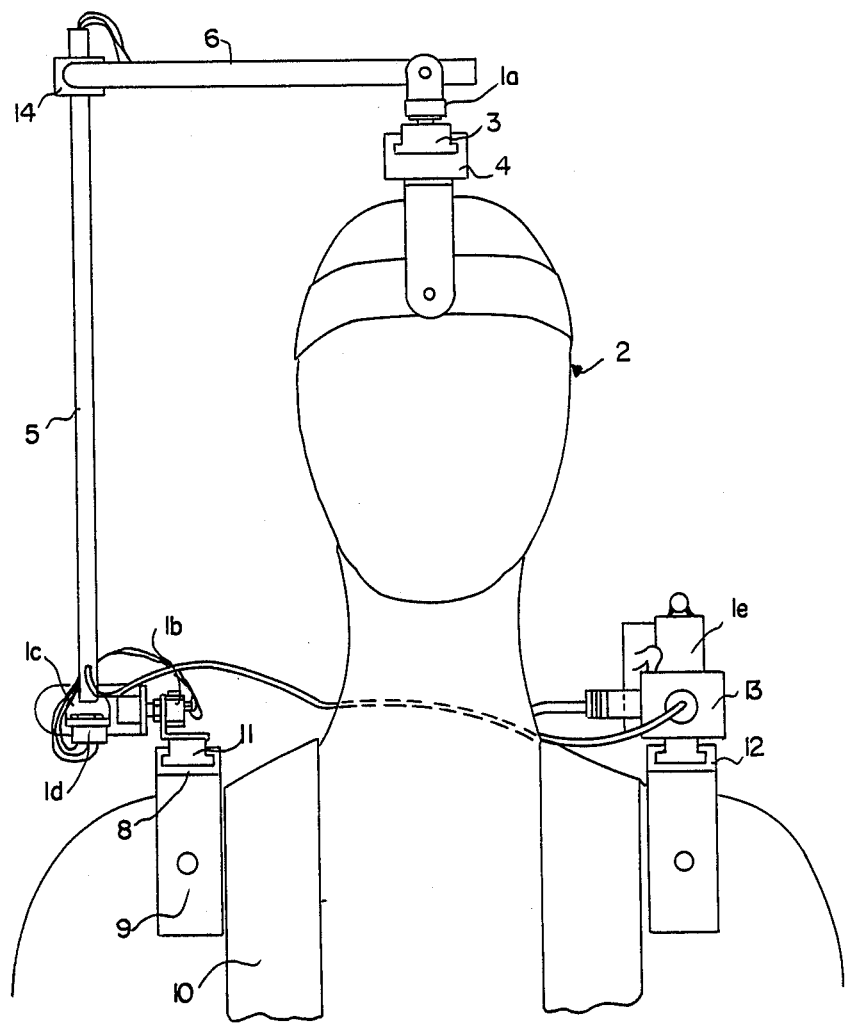
FIGS. 2-5 show an embodiment of the measuring device according the invention, seen from different views.
Figure 3:
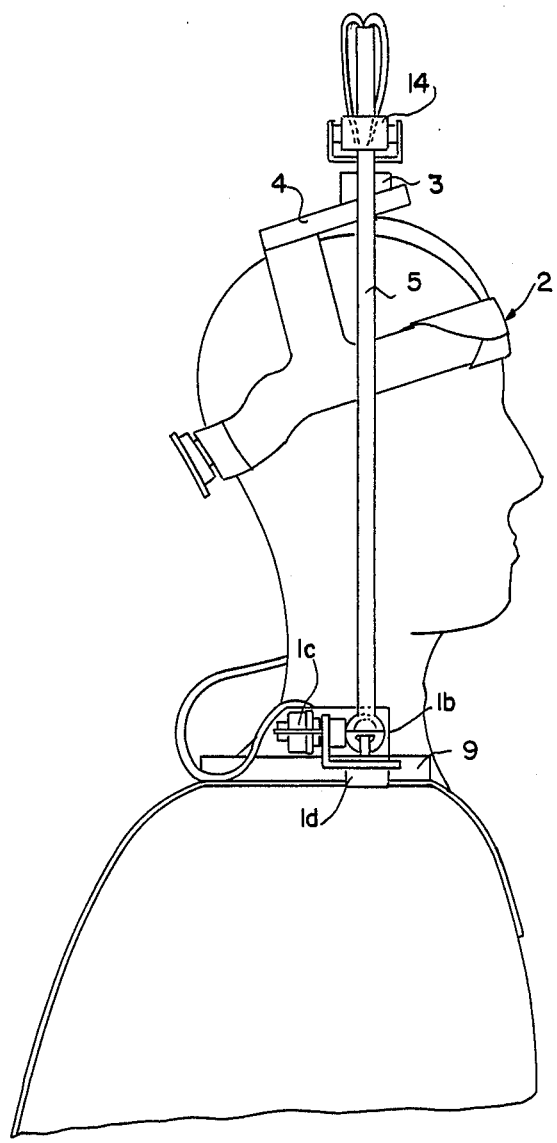
Figure 4:
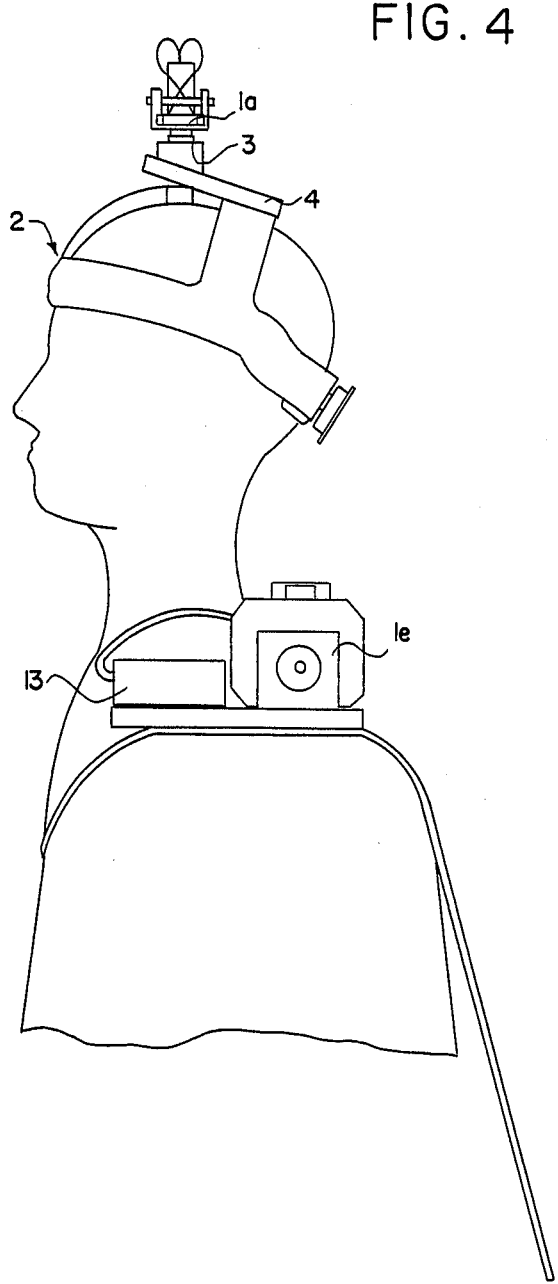
Figure 5:
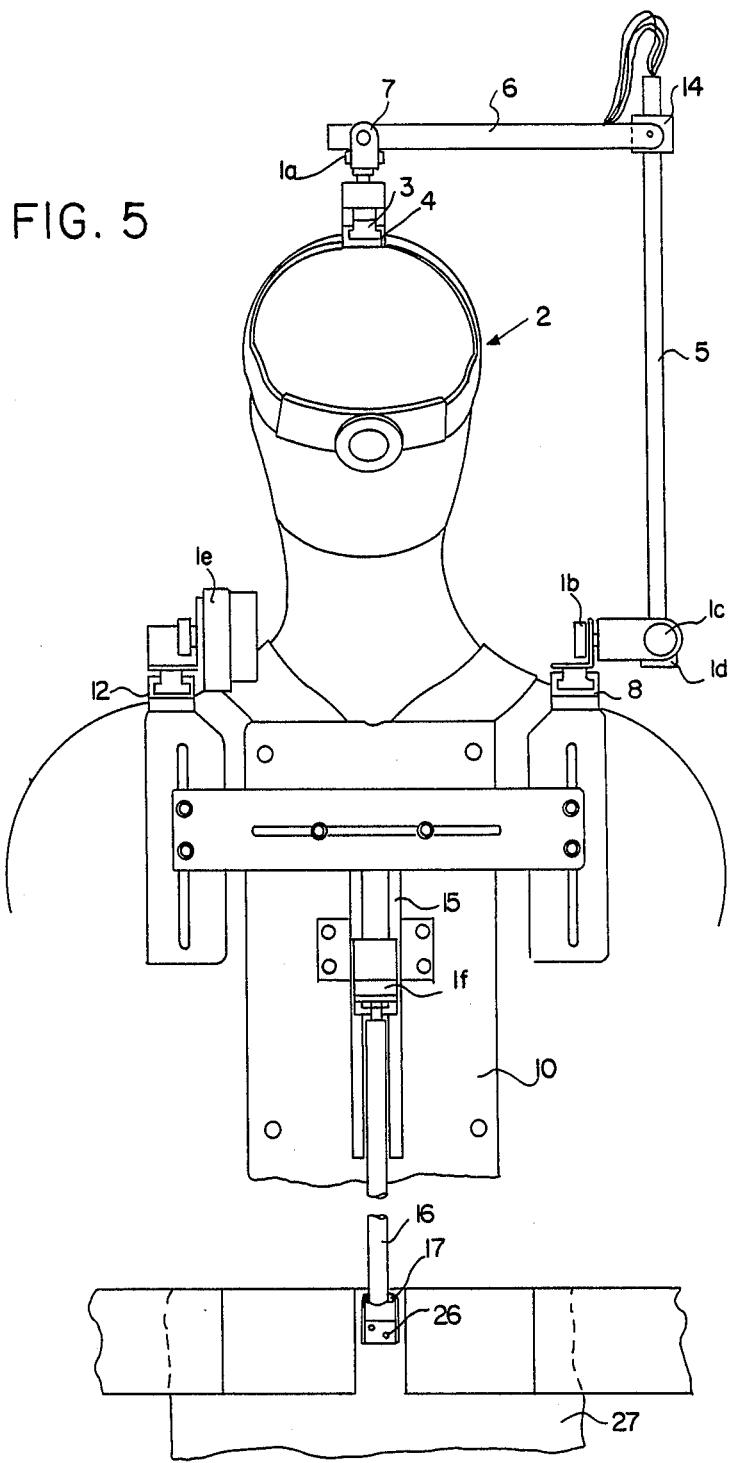

The invention relates to a device for detection/measurement of relative movements or positions of a part of the body. In FIGS. 1(a–f) are illustrated examples of bendings of the back and the head, which the present invention is arranged to detect. FIGS. 1(a–c) present from right to left the flexion and the extension of the head i.e. the bending forward and backward, lateral flexion, and rotation. FIGS. 1(d–f) from right to left show lateral flexion of the back, its flexion, i.e. bending forward, and its rotation. The device detects also the time during which the present part of the body takes a certain position or angle.

FIGS. 2–5 show from different views the measuring device comprising a transmitter means which consists of potentiometers, and transfer means, which adjust the potentiometers according to the relative position of the head with respect to the rest of the body.

The head's rotation is measured with a potentiometer 1a placed on a helmet 2 to be secured on the head of the test person. The potentiometer 1a is connected to a potentiometer holder 3 which can be adjusted along a rail 4 in the helmet 2, so that the potentiometer 1a is located straight above the coronal suture.

The head's extension/flexion is measured with a potentiometer 1b placed in a so called potentiometer joint, where also a potentiometer 1c for measuring the lateral flexion of head and a compensation potentiometer 1d is arranged. The object of the compensation potentiometer 1d is to compensate the discrepancy in the rotation measurement, when the shoulder is raised or moved forward/backward.

On the compensation potentiometer 1d there is placed a rotary bar 5, which is pivotally connected to a bar 6, which in its turn is pivotally connected to the housing of the rotation potentiometer 1a in such a manner that a parallelogram action linkage is achieved, wherein the vertical centre line of the head make one part, and the imaginary axis about which the head's flexion and extension takes place is another part.

The potentiometer joint with the potentiometers 1b, 1c and 1d are placed in a rail 8 which is arranged on an yoke 9 intended to be fastened on the test person's shoulders by means of a harness 10. The position of the potentiometer joint 1b–d is adjustable along the rail 8 by means of a holding means 11.

The flexion of the back is measured with an inclinometer 1e, e.g. a pendulum sensor, placed on the yoke 9 on the opposite shoulder with respect to the potentiometer joint 1b–d in a rail 12. A collecting box for the electrical connections is indicated by 13. Another inclinometer (not shown) for measuring the shoulder's lateral flexion can also be arranged here, which inclinometer is turned 90° in relation to the inclinometer 1e.

The rotation of the back relative to the pelvis is measured by means of a potentiometer 1f which is displaceable in a rail 15 on the harness 10. A longitudinal line of the rail 15 should be substantially parallel with the spine. To the axle of the potentiometer 1f there is attached a flexible axle 16 which through a balljoint 17 is connected with a plate 26 fixed on a pair of trousers 27, so that the plate 26 is placed just on top of the spine of the pelvis. By the fact that the potentiometer 1f is displaceable along the rail 15 the elongation of the back when bent is taken up.

The measuring device is applied on the test person in the following manner: The yoke 9 is placed on the shoulders and is secured by means of the harness 10. The holding means 3 of the potentiometer 1a is adjusted so that its upper surface becomes horizontal and its position is adjusted along the rail 4 so that the center of the potentiometer 1a is placed just above the coronal suture (which corresponds to the auditory meatus) after which it is fixed.

The potentiometer joint 1b–d is applied in the rail 8 on the right shoulder (according to the drawings). The inclinometer 1e and the collecting box 13 are placed in the rail 12 on the left shoulder (according to the drawings) as far back as possible and are then fixed. The inclinometer 1e is adjusted to horizontal position and fixed.

The bar 5 of the potentiometer joint has a square or another non-circular cross-section and is connected to the bar from the helmet by being passed through a bushing 14 rotatably mounted to the bar 6, said bushing having an axial hole which has a cross-section corresponding to the bar 5. The potentiometer joint 1b–d is adjusted along the rail 8 so that the bar 5 is situated vertically and just opposite the auditory meatus. The bar 5 is thereby displaced in the bushing 14 so that a right angle is provided in relation to the bar 6, whereby its location in the bushing 14 is fixed. The bar 5 can of course also have a round cross-section and be fixed to the bushing 14 in an appropriate way.

The electrical coupling

Figure 6:
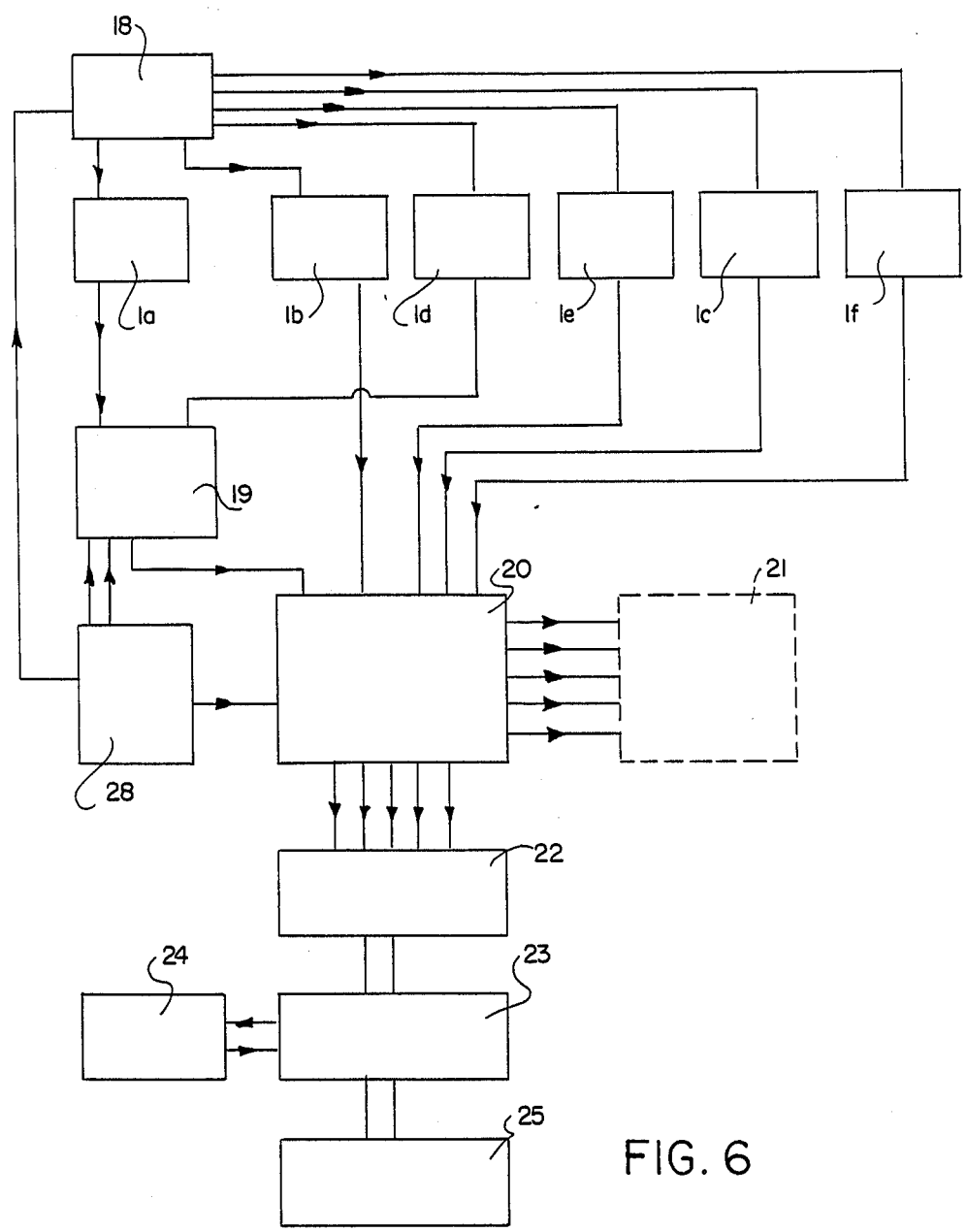
FIG. 6 shows schematically a block diagram of the invention.

The signals from the measuring sensors 1a–f are transferred to an electronic transducer or processing device. This can comprise e.g. a known device such as a computer which receives, stores and processes the incoming measuring data. In the circuit diagram, schematically shown in FIG. 6, the paths of the signals from the sensor 1 (a–f) to the results written by a printer are shown. Examples of print-outs from the system are shown in FIGS. 8(a–g).

To all sensors 1(a–f) a feeding power from an accumulator 28 and a constant voltage set is supplied, here called a sensors feeding aggregate 18. The signals from the sensor 1a and 1d, i.e. the sensors for measuring the rotation of the head and the compensation potentiometer, are transferred to a differential amplifier 19 which detects the difference between the signals, and thereby also detects the rotation of the head with respect to the back.

Signals from the sensors 1b, c, e, f and from the differential amplifier 19 are sent to a junction box 20, from which signals can be transferred to an instrument tape recorder or a printer 21 for storage and later analysis.

The junction box 20 is also electrically connected to an analogue/digital converter 22, i.e., an A/D-converter, in which the analogue signals from the measuring sensors 1(a–f) are converted to digital signals which thereby are readable by a computer 23. The computer can e.g. have the program stored on a tape recorder 24. In the computer 23 an internal memory is arranged. The computer 23 is suitably connected to a printer 25 for printing of the measuring results.

Every measuring sensor 1(a–f) connected to the measuring circuit is detected several times each second. The electronics is so arranged that it only registers when a data value has been detected several times, i.e. the electronics discriminates all measured data which have occurred during the "building-up time" of the measuring sensor. Independent of this process, a data value is registered every second. However, the analogue signal is sent to and stored in the instrument tape recorder 21.

Processing of the measuring data

Figure 7A:
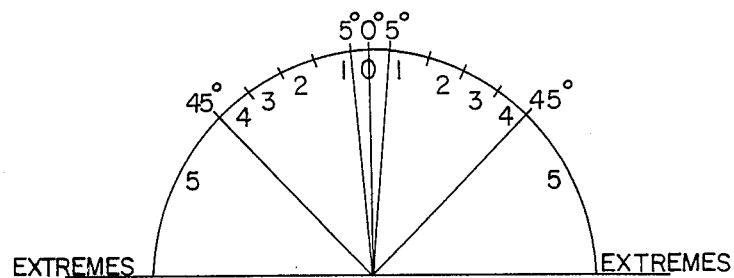
FIG. 7a shows an example of the measuring area for head rotation, extension/flexion and lateral flexion.

In FIGS. 8a–8g are shown examples of print-outs from a measurement performed by the device according to the present invention. Referring to FIG. 7a, the head's rotation is measured according to two 90° sectors with 0° being taken straight forward. The total 180° range is graded into smaller sectors according to FIG. 7a. The left sector corresponds to the upper registrations on the tape according to FIG. 8(d).

The measuring area for the head's extension/flexion is divided in the same way as for the rotation (FIG. 7a), but with the difference that extreme values are situated above 65°. The flexion corresponds to the upper registrations on the registration tape in FIG. 8(c).

The measuring area for the lateral flexion is the same as for the extension/flexion. Left lateral flexions (FIG. 7a as just explained) corresponds to the upper registrations on the tape in FIG. 8(b).

Figure 7B:
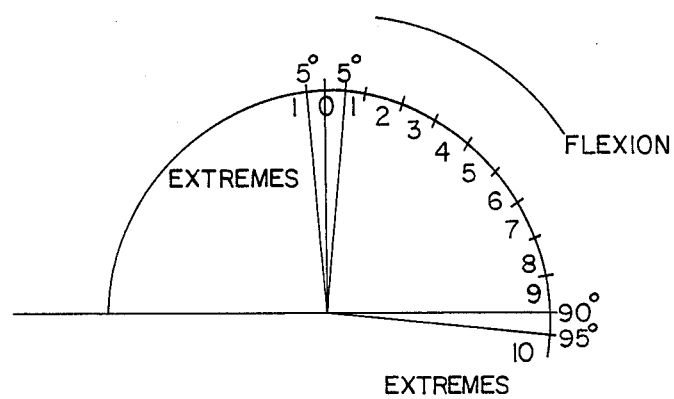
FIG. 7b shows an example of the measuring area for bending of the back.

Back bendings are measured according to a +5°—−95° range with 0° being taken as straight up. The gradings of the range are presented in FIG. 7b (see FIG. 8a).

Figure 7C:
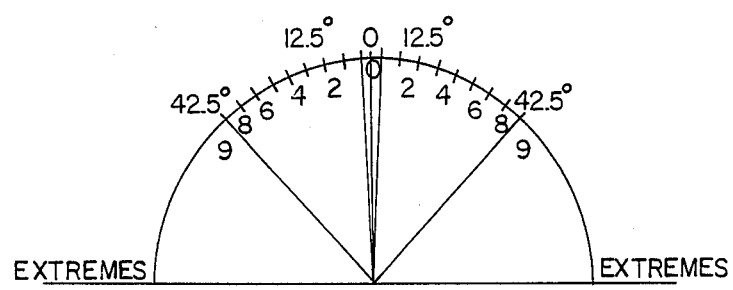
FIG. 7c shows an example of the measuring area for rotation of the back.

The rotation of the back is measured according to a 85°-range with 0° being taken as straight forward. The gradings of the range are presented in FIG. 7c (see FIG. 8f).

Each of FIGS. 8a–8d and 8f shows the right print consisting of a register of the measuring results obtained in a series of measurements. At the top, facts about the test person may be written, e.g., name, social security number and so on. Underneath, a table is presented where the number of time intervals a certain position. For example the back's bending position in FIG. 8a, has been taken. On the left is a histogram which graphically illustrates the frequency of the different positions. From the table and the histogram one can estimate how injurious the respective working movement is.

Figure 8A:
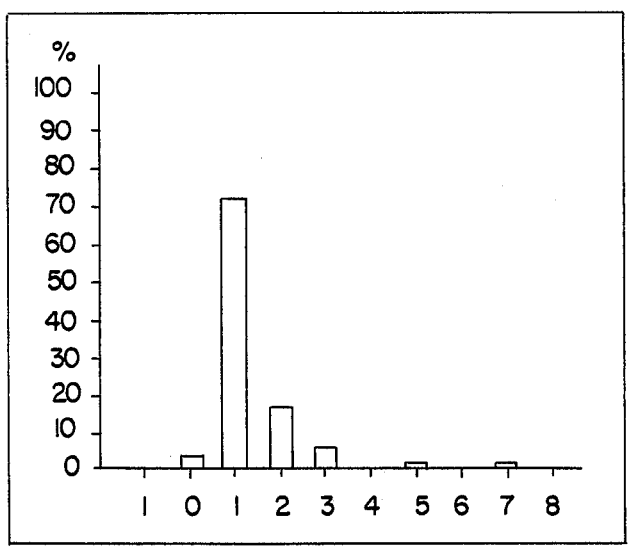
Figure 8B:
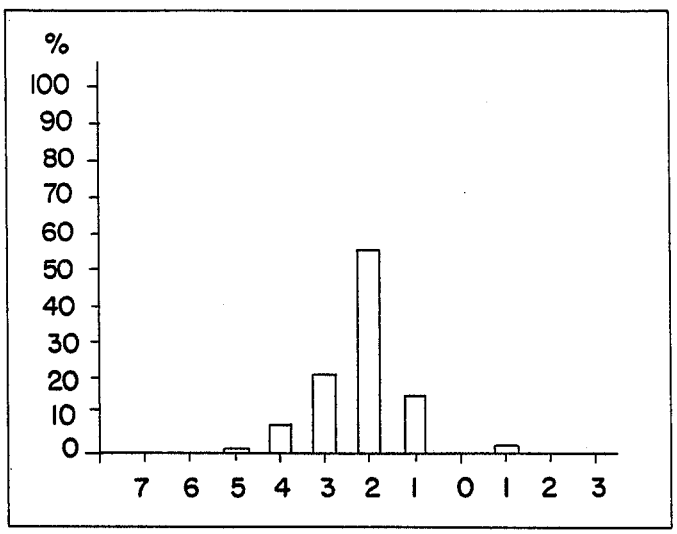
Figure 8C:
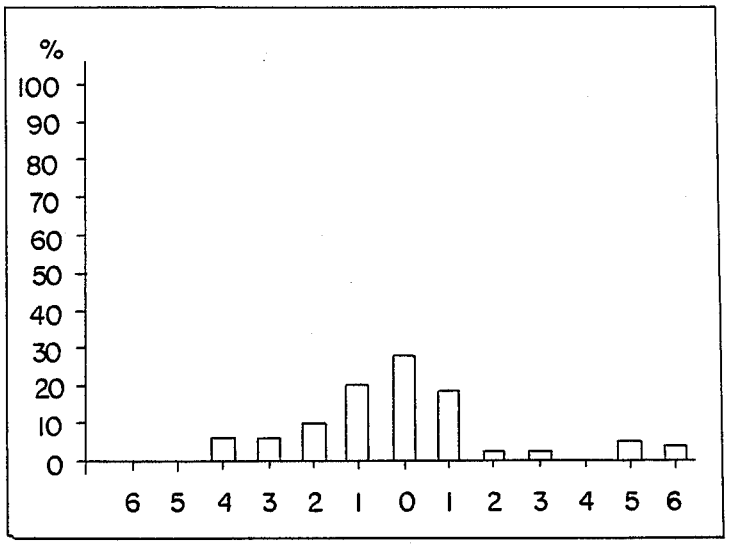
Figure 8D:
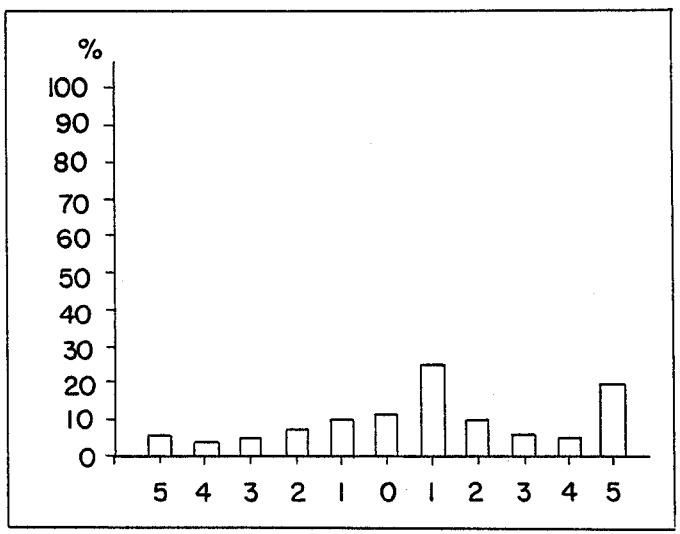
Figures 8E, 8F:
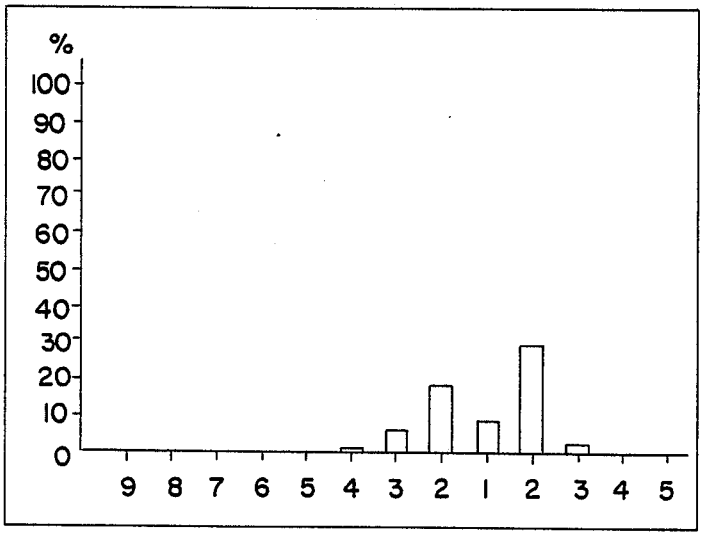

The table and histogram in FIG. 8b are those in FIG. 8a, constructed as but show the result of the measurements of head lateral flexion. FIGS. 8c and 8d present similar data for head flexion and head rotation, respectively, and the data in FIG. 8f relate analogously to back rotation. The matrix of data in FIG. 8e shows the number of simultaneous occurrences of certain positions with respect to both the head's extension/flexion and its rotation FIG. 8g shows a similar matrix of data with respect to both back rotation and flexion.

The invention is of course not limited to the above described embodiments. Rather, various alternative embodiments are possible within the scope of the claims. It is also possible to adapt the present invention to detect the position of motions of other parts of body, e.g. the arms.

I claim:

1. A device for simultaneously measuring relative movements and positions of parts of a human body comprising:
    at least two measuring sensors; and attachment means for attaching said sensors to the parts of the body whose relative movements and positions are to be measured; and
    at least two bars which are pivotally connected to each other and interconnect said means for attaching the sensors to the parts of the body, said bars forming a part of a pivotal parallelogram action linkage and the imaginary axes about which said movements are performed forming another part of said pivotal parallelogram action linkage; said measuring sensors being arranged at vertices of said pivotal parallelogram action linkage;
    said attachment means being for attaching a first one of said at least two measuring sensors to the head of the body for measuring the head's rotation; and for attaching a second one of said at least two measuring sensors to a shoulder of the body; a first one of said bars thereby being pivotally connected with the measuring sensor on the head, said first bar at its opposite end being pivotally connected with a second one of said bars, and the measuring sensor on the shoulder being arranged at the vertex at the opposite end of said second bar remote from its pivotal connection with the first bar.

2. A device according to claim 1, further comprising third and fourth measuring sensors; and attachment means for attaching said third and fourth sensors to the shoulder at said vertex at said opposite end of said second bar, for respectively measuring the head's extension/flexion, and the head's lateral flexion.

3. A device according to claim 2, wherein the three above-mentioned sensors on the shoulder are comprised in an integrated shoulder unit, said shoulder unit also comprising a compensation potentiometer means for compensating any discrepancy in head rotation, extension/flexion or lateral extension/flexion measurements when the shoulders are raised, lowered, or moved forward or backward.

4. A device according to claim 2, further comprising at least a fifth measuring sensor; and attachment means for attaching said fifth sensor to the opposite shoulder of the body for detection of the back's flexion and/or lateral flexion.

5. A device according to claim 4, wherein said attachment means for attaching said measuring sensors to the body comprise holders for holding the sensors, the holders being displaceable along respective rails which are attachable to the body.

6. A device according to claim 5, wherein the holder for holding the first sensor to the head is displaceable along a rail, which is attached to helmet means for being worn on the head.

7. A device according to claim 5, wherein said holders for holding the second, third, fourth, and fifth sensors are displaceable along rails which are attached to a harness which is for being worn on the shoulders.

8. A device according to claim 4, further comprising at least a sixth measuring sensor; means for attaching said sixth sensor to the back of the body adjacent the spine; and transmission means for transmitting rotational motion to said sixth sensor from means fixable to the pelvis area; for measuring rotation of the back with respect to the pelvis.

9. A device according to claim 8, wherein said sixth measuring sensor is displaceable along a rail on a harness which is attachable to the shoulders, said rail being arranged substantially parallel with the spine.

* * * * *